(12) United States Patent
Marino (10) Patent No.: US 6,547,746 B1
(45) Date of Patent: Apr. 15, 2003

(54) METHOD AND APPARATUS FOR DETERMINING RESPONSE THRESHOLDS

(76) Inventor: Andrew A. Marino, P.O. Box 127, Belcher, LA (US) 71004

( * ) Notice: Subject to any disclaimer, the term of this patent is extended or adjusted under 35 U.S.C. 154(b) by 0 days.

(21) Appl. No.: 09/940,696

(22) Filed: Aug. 27, 2001

(51) Int. Cl.[7] .............................. A61B 5/05; A61B 5/04
(52) U.S. Cl. ........................ 600/554; 600/545; 600/544; 600/546
(58) Field of Search .............................. 600/545, 544, 600/546, 554, 555, 558, 559, 300

(56) References Cited

U.S. PATENT DOCUMENTS

| | | |
|---|---|---|
| 4,201,224 A | 5/1980 | John |
| 4,214,591 A | 7/1980 | Sato et al. |
| 4,275,744 A | 6/1981 | Thornton et al. |
| 4,462,411 A | 7/1984 | Rickards |
| 4,493,327 A | 1/1985 | Bergelson et al. |
| 4,699,153 A | 10/1987 | Shevrin et al. |
| 4,736,751 A | 4/1988 | Gevins et al. |
| 4,763,666 A | 8/1988 | Strian et al. |
| 4,913,160 A | 4/1990 | John |
| 5,083,571 A | 1/1992 | Prichep |
| RE34,015 E | 8/1992 | Duffy |
| 5,137,027 A | 8/1992 | Rosenfeld |
| 5,143,081 A | 9/1992 | Young et al. |
| 5,282,475 A | 2/1994 | Urbach et al. |
| 5,381,805 A | 1/1995 | Tuckett et al. |
| 5,673,703 A | 10/1997 | Fisher et al. |
| 5,788,648 A | 8/1998 | Nadel |
| 5,816,247 A | 10/1998 | Maynard |
| 5,860,936 A | 1/1999 | Levin |
| 6,051,209 A | 4/2000 | Metz et al. |
| 6,304,775 B1 * | 10/2001 | Iasemidis et al. ........... 600/544 |

OTHER PUBLICATIONS

Eckmann, J.–P., et al., "Recurrence plots of dynamical systems," *Europhysics Letters*, vol. 4 (1987), pp. 973–979.

Webber, Jr., C. L., et al., "Dynamical assessment of physiological systems and states using recurrence plot strategies," pp. 965–973.

Elbert, T., et al., "Chaos and physiology: Deterministic chaos in excitable cell assemblies," *Physiol. Rev.*, vol. 74(1) (1994), pp. 1–47.

Zbilut, J. P., et al., "Recurrence quantification analysis and principal components in the detection of short complex signals," *Physics Letters A*, vol. 237 (1998), pp. 131–135.

* cited by examiner

*Primary Examiner*—Max F. Hindenburg
*Assistant Examiner*—Navin Natnithithadha (57) ABSTRACT

A method and apparatus for evaluating the response of a biological or nonbiological system to an external or internal stimulus (optical, thermal, auditory, tactile, taste, electrical, magnetic, chemical, biochemical, pharmacological, hormonal, internal cellular transformations, etc.). The system is exposed to the stimulus while at least one electrophysiological signal is recorded. The recorded data is digitized, stored, and analyzed using RQA or other suitable techniques to ascertain the properties of the system's response to the stimulus.

30 Claims, 6 Drawing Sheets

METHOD AND APPARATUS FOR DETERMINING RESPONSE THRESHOLDS

BACKGROUND OF THE INVENTION

1. Field of the Invention

The present invention relates to a method and apparatus for quantifying the response thresholds of biological and nonbiological systems to stimuli. In particular, the present invention relates to the determination of response thresholds using Recurrence Quantitation Analysis and other mathematical techniques, for perceivable and nonperceivable stimuli (light, sound, temperature, pressure, aroma, chemical, biochemical, learning tasks, electric and magnetic fields, and so forth).

2. Discussion of Background

Biological systems—ranging from cells in culture media to laboratory animals to human beings—exhibit dynamically complex responses to stimuli. The classic approach to studying stimulus-response relationships has been to present the stimulus in a simplified experimental setting, with as few variables as possible, and record the subject's response. Various physiological parameters were also measured in order to provide an objective measure of the subject's response, including skin resistance and potential, blood pressure, respiration rate, electrocardiogram (ECG or EKG), electroencephalogram (EEG), electromyogram (EMG), etc. This approach was historically useful in determining thresholds for readily-perceivable stimuli such as light, sound, and pressure, as well as other stimuli that were specifically identifiable and recognizable as stimuli. However, the classic methodology fails when the stimulus is one that the subject does not perceive directly, or which does not lend itself to association with straightforward measurements of physiological parameters.

Recent developments in the study of physiological systems (including humans) draw on chaos theory and informational theory, suggesting that these are complex systems that exhibit equally complex dynamic, state-dependent behaviors. Unlike classic physiology, which implicitly assumed that physiological systems are both linear and homeostatic, the new paradigm acknowledges that the experimenter's underlying assumptions can affect both the design and the outcome of any experimental study. (For purposes of this specification, the term "homeostatic" refers to the tendency of a biological system to maintain internal constancy regardless of its surrounding environment. "Nonhomeostatic" is the reverse of homeostatic.) This approach has led to the development of new mathematical tools for the study of complex, nonlinear behaviors in biological systems.

Many different types of stimuli entail physiological changes that are straightforward to measure and analyze. For example, thresholds of perception for light, sound, and pressure are measured by standard, well-established techniques. Similarly, the effects of medications on blood pressure, blood chemistry, heart rate, etc. can be measured with readily-available instrumentation, and can be analyzed using familiar statistical techniques. The difficulty arises in measuring the effects of stimuli that elicit nonlinear, non-homeostatic responses. Many environmental parameters are believed to elicit such nonlinear responses, including but not necessarily limited to electric and magnetic fields, light, and sound.

Various approaches to the study of stimulus effects have been developed. By way of example, Metz, et al. (U.S. Pat. No. 5,051,209) measures the effects of external stimuli on the brain using positron emission topography (PET). Stimuli include psychoactive compounds, drugs, and sensory-perceivable environmental factors (temperature, noise, vibration, light). The method includes the following steps: while controlling behavioral influences on the subject's brain via a "behavioral clamp," (1) measuring cerebral metabolism with a positron emission tomography (PET) scan in the absence of external treatment; (2) administering an external treatment to the subject, (3) measuring cerebral metabolism after the treatment, and (4) determining any differences between the cerebral metabolism in steps (1) and (3). The PET image sets are standardized so the data from different subjects, and from the same subject at different times, can be compared to determine which (if any) brain areas show differences between the treatment conditions.

Electroencephalographic (EEG) measurements are frequently used to study responses to various stimuli. By way of example, Levin (U.S. Pat. No. 5,860,936) provides a differential geometric method and an apparatus for measuring an observer's perception of dynamically evolving visual and auditory stimuli. The apparatus includes a stimulus output device for presenting stimuli to the observer, and a stimulus manipulation device that permits the observer to modify the presented stimuli by selecting related stimuli from a database. The method is based on the concepts of "reference stimuli" and "reference transformations": an evolving stimulus is described in terms of an initial reference state and of reference transformations (for example, movement in a certain distance for a certain direction, change in color, etc. The observer is asked to identify which small transformation of a first stimulus is perceived to be equivalent to a small transformation of a second stimulus. The observer's perceptions of a number of such transformations are used to calculate an affine connection on the stimulus manifold, which encodes how that particular observer perceives evolving stimuli as sequences of reference transformations. Differences between observers characterize differences between their individual perceptions, and can be used to "translate" sets of stimuli between observers).

Maynard (U.S. Pat. No. 5,816,247) uses neural networks to analyze EEG data with an apparatus that includes circuitry for receiving, amplifying and processing EEG signals, a computer for statistical processing of the signals, a neural network with a training mode and a classifying mode, a display for displaying the output classifying values in n-dimensional form, and a memory for storing the data. The method includes the following steps: (1) obtaining sets of training data from a plurality of patients; (2) determining categories for classifying the sets; (3) defining an n-dimensional space in which the determined categories are represented as distinct coordinates; (4) training a neural network with n outputs using the sets as input data and the defined categories as target outputs; and (5) applying a set of EEG data from a patient to the neural network to derive a position in the n-space for the purpose of assessing a patient category.

Nadel (U.S. Pat. No. 5,788,648) shows an EEG apparatus for exploring a subject's response to quantifiable external stimuli (oral, visual, tactile, acoustic, and/or olfactory, and combinations thereof). The apparatus includes sensing apparatus for sensing brainwave signals, stimulating apparatus for generating the stimuli, and processing apparatus for receiving and processing the signals to compute a correlation quotient of the signals and the stimuli. Data analysis is based on Fourier transforms.

Urbach, et al. (U.S. Pat. No. 5,282,475) disclose an apparatus and method for objective determination of auditory thresholds for intelligible speech. The apparatus includes a microprocessor, a digital-to-analog converter and a signal amplifier for presenting a randomly-selected speech stimulus to a human subject, a multichannel EEG amplifier for monitoring the physiological response of the subject, and a CRT display. The stimulus is presented to the subject through earphones while monitoring the EEG, and recorded data are corrected for eye movement artifacts.

Rosenfeld (U.S. Pat. No. 5,137,027) provides a method for using event-related potentials (P300 brain wave amplitude and/or latency) to evaluate whether or not a subject has previously performed a given act. Subjects are exposed to two successive groups of perceivable stimuli, each group designed according to a specified protocol. The following parameters are computed and compared for the two stimulus groups: (1) the prestimulus EEG potential for a first measured time interval (50–500 msec); and (2) the maximum voltage amplitude of the P3 wave produced over a second time interval (also 50–500 msec), where the P3 wave is measured within 300–1200 msec from the start of exposure to the stimulus.

Prichep (U.S. Pat. No. 5,083,571) discloses a system for using discriminant analysis of EEG data for diagnostic purposes, specifically, to automatically evaluate the probability that a patient belongs to a specified diagnostic category (or a subtype within a category). The EEG data is processed via standard techniques to obtain factor Z scores which are used to distinguish among different clinical conditions via discriminant analysis.

John applies factor analysis and Z-transformations to EEG data. U.S. Pat. No. 4,913,160 deals with the measurement of averaged evoked responses (AERs) while presenting a programmed sequence of stimuli to a subject. The AERs are analyzed using factor analysis, where each waveshape is digitized, decomposed by factor analysis, Z-transformed and compared to results from a normal population. Results are displayed as color-coded topographic maps of the head showing the locations of the electrodes (different colors represent the degree of abnormality reflected by the Z-scores). U.S. Pat. No. 4,201,224 describes a method and system for the quantitative description of human abnormal brain states. EEG data is recorded while a multimodal stimulator provides signals aimed at different sensory systems (clicks, flashes, etc.). The patient's data are processed and compared with previously stored normative data that describe brain states in patients without head trauma. Data processing includes a set of Z-transformations that define a brain state vector: the length, direction a n change of this vector over time provide an evaluation of the anatomical location of any brain damage, the severity of functional impairment, and the rate of improvement or deterioration of the patient's state.

Gevins, et al. (U.S. Pat. No. 4,736,751) provide a method and system for statistical analysis of brain wave activity (evoked potentials) using a fairly large number of scalp electrodes. The locations of the electrodes are digitally recorded and stored in computer memory, then the subject is exposed to a set of stimuli while recording brain waves, magnetoencephalographic waves, and eye movement data. These data are analyzed to determine the brain sites which give rise to the activity; data can be displayed on a three-dimensional model. The signal-to-noise ratio is improved by eliminating data with excessive noise contamination, using bandpass filters, and spatial deconvolution analysis to reduce the distortion of brain waves due to transmission through the cerebrospinal fluid, skull, and scalp.

Shevrin, et al. (U.S. Pat. No. 4,699,153) use a form of nonperceived stimulus (subliminal images) to assess verbal psychobiological correlates with EEG data. The stimulus consists of a plurality of words which are selected to be in four categories (pleasant words, unpleasant words, words related to a diagnosed conscious pathological condition, and words related to a diagnosed unconscious pathological condition). The words are presented by tachistoscope in both subliminal and supraliminal modes of operation (1 msec and 30 msec duration, respectively). Evoked responses are analyzed using a technique based on information signal theory).

Bergelson, et al. (U.S. Pat. No. 4,493,327) disclose a method and system for automatic evoked potential detection. The method consists of deriving sets of averaged brain waveforms in the presence and absence of a stimulus, computing (via Fast Fourier Transform or FFT) a test measure that is related to the averaged spectral characteristics and variance of each set, and evaluating the test measures to ascertain the likelihood that the:patient exhibited a significant evoked potential in response to the stimulus.

Sato, et al. (U.S. Pat. No. 4,214,591) provide a brain wave analyzing system and method for automatically identifying a spectrum pattern obtained by autoregressive model analysis. The method relies on the fact that brain waves include a part that is connected with some past activities of the brain and a part that is not. A series of standard brain waves are measured, digitized, and processed to obtain the mean and variance vectors of the autoregressive coefficient vectors of the digital data. The brain waves to be examined are processed in the same fashion. The distances between the vectors of the experimental and standard brain waves are then compared.

Duffy (U.S. Pat. No. Re. 34,015) generates topographic displays derived from EEG data (evoked potentials resulting from pseudorandom stimuli) for the purpose of diagnosing brain disorders. The EEG data is digitized and transformed to spectral data via FFT. Data reflecting movement artifacts and high frequency noise are eliminated, and the reduced data is topographically displayed. The data can be analyzed using significance probability mapping to identify significant brain activity features related to various neurophysiological conditions, grid sector analysis to produce numerical measures of the degree of global or focal deviations from normal, and coefficient of variation analysis to find head regions where there are wide variations in brain activity.

Rickards (U.S. Pat. No. 4,462,411) measures auditory responses with an evoked response audiometer that supplies a signal modulated by a continuous frequency waveform in order to evoke phase-locked steady state potentials in the subject. The subject's EEG is recorded, analyzed using Fourier transforms, and the relevant spectral components are used to measure the degree of hearing loss.

Thornton, et al. (U.S. Pat. No. 4,275,744) disclose an auditory response detection method and apparatus that uses tone burst signals. Their system is based on the observation that observations of the EEG signal made at selected intervals following an auditory stimulus can provide a statistical estimate of the likelihood of a response being actually present in an individual subject. The EEG data is monitored, filtered to remove frequencies above and below the range of interest, and sampled at predetermined times after the auditory signal has been applied to the subject. The apparatus provides an output signal when the polarity of the sample signal matches the expected polarity at the predetermined times.

Fisher, et al. (U.S. Pat. No. 5,673,703) describe an apparatus and method for automated testing of vibrotactile responses. The apparatus includes a computer-controlled stimulation probe that applies a steady, reproducible stimulus; the computer also records the subject's response.

Tuckett, et al. (U.S. Pat. No. 5,381,805) disclose a computerized apparatus for testing cutaneous responses to heat, pricking, indentation, vibration, and two-point discrimination. A programmable computer controls the operation and the apparatus and records the patient's responses.

Young, et al. (U.S. Pat. No. 5,143,081) apply a train of paired stimuli to a biological system, and measure and analyze the response. The first of each pair of stimuli (the conditioning stimulus) is applied at randomly varying intensities and at a constant frequency; the second of each pair (the test stimulus) is applied at a constant intensity and a randomly varying frequency. Measurements can be made on the neural, cardiovascular, skeletal muscle, visual, auditory, secretory, renal, hepatic, gastrointestinal, and genito-urinary systems.

Strian, et al. (U.S. Pat. No. 4,763,666) provide a method and apparatus for determining the thermal sensitivity or pain threshold. Their method consists of establishing upper and lower temperature limits for perceived pain, then applying random-temperature thermal stimuli to the skin to verify the reported pain thresholds.

Additional techniques such as recurrence quantitation analysis and principal components analysis have been developed to aid in the detection of signals in data sequences, especially nonlinear or chaotic signals that are not amenable to traditional linear analysis. These techniques are described in the following publications, which are incorporated herein by reference: "Recurrence quantification analysis and principal components in the detection of short complex signals," J. P. Zbilut, A. Giuliani & C. L. Webber, Jr., *Physics Letters A*, Vol. 237 (1998), pp. 131–135; "Dynamical assessment of physiological systems and states using recurrence plot strategies," C. L. Webber, Jr. & J. P. Zbilut, *J. Applied Physiology*, Vol. 76 (1994), pp. 965–973. These techniques permit identification and analysis of time correlations ("recurrences") in physiological data that are not apparent in the time series measurements.

Despite the many different techniques available to researchers, there remains a need for a reliable methodology for determining the thresholds of physiological stimuli, whether or not the stimuli are perceived by the subject.

SUMMARY OF THE INVENTION

According to its major aspects and broadly stated, the present invention includes a method and apparatus for evaluating the response of a subject (or other biological or nonbiological system) to an external stimulus (optical, thermal, tactile, auditory, taste, electrical, magnetic, pharmacological, hormonal, chemical, biochemical, etc.) or to a stimulus that is generated internally (local changes in oxygen concentration, transformation; of cells from normal to malignant, localized tissue injury, localized inflammation, etc.). The subject is exposed to the stimulus while at least one electrophysiological signal (EEG, EKG, EMG, electrical potential, blood oxygen saturation, etc.) is recorded. The recorded data is digitized, stored, and analyzed to ascertain the properties of the subject's response to the stimulus. The significance of the results can be analyzed using parametric or nonparametric statistical procedures. The method is independent of well-known constraints such as the size of the data set, underlying assumptions regarding the statistical distribution of the data, and assumptions about the nature of the data (homeostatic vs. nonhomeostatic, linear vs. nonlinear, etc.). It permits reliable analysis of a subject's response regardless of whether or not the subject is aware of the presence (or absence) of the stimulus being evaluated, and regardless of whether the stimulus is external or internal. Furthermore, the invention permits detection of structure in signals whether or not the signals were elicited by periodic or nonperiodic stimuli.

The apparatus (to be described in detail below) may include equipment for generating stimuli, recording output signals from the subject, and recording, processing, and analyzing the output signals. Unwanted portions of the measured output signals (for example, the relatively high-amplitude signals associated with the subject's EMG and respiration that appear during measurements of the subject's EEG) are removed by a numerical filter or other suitable filter. The apparatus also includes a phase-space filter that removes non-useful portions of the output signals in phase space, an analog-to-digital (AID) converter, and a programmable computer for carrying out recurrence procedures that further facilitate analysis of the data.

The invention can be used with either controlled or uncontrolled stimuli (also termed "inputs"). Importantly, it permits reliably distinguishing the subject's response in the form of an output signal of interest from other, generally stronger, signals that may obscure it. For example, the voltage from a surface electrode placed on a selected location on a subject's skin can be measured over a period of time. When these measurements are analyzed, the voltage shows a trend (either up or down) that is related to electrode polarization effects. In addition, there is an approximately periodic signal that corresponds to the subject's heart beat (the EKG or ECG), signals that correspond to the subject's brain electrical activity (EEG), rhythmic signals that correspond to the subject's breathing, and episodic signals that can be traced to contractions of the subject's muscles during movement (EMG). Selected signals of this nature can be optimized depending on the placement of the electrode, the choice of frequency measured, and other well-known factors. In contrast, the invention. permits isolation of much smaller (usually by several orders of magnitude) electrical signals that represent the subject's response to a stimulus of interest.

An important feature of the present invention is the use of Recurrence Quantification Analysis ("RQA") or other suitable techniques to evaluate the output signals. Such techniques can be used to quantify and analyze nonhomeostatic responses to a variety of external and internal stimuli, including but not limited to light, sound, pressure, aroma, taste, electric and magnetic fields, chemical, biochemical, and hormonal stimuli, and internal changes on the cellular level. RQA, for example, involves digitizing the recorded data to obtain a scalar time series, which is then embedded in a multidimensional state space using a time delay to obtain a diagram that represents the evolution of the state of the system over time. This technique is particularly suitable for the study of systems that are characterized by nonhomeostatic transients and state changes.

Another important feature of the present invention is the use of numerical and phase-space filters to remove non-useful portions of the output signals. A numerical filter removes selected amplitudes, frequencies, or other components of the output signal; a phase-space filter removes selected points in phase space. Application of these filters prepares the data for recurrence analysis and increases the overall sensitivity of the analysis.

Another important feature of the invention is the apparatus used to implement the method. The apparatus may include equipment for generating a stimulus ("controlled input"), measuring output signals from the subject, and storing and analyzing the resulting data. Depending on the nature of the system being examined, analyses may include parametric or nonparametric statistical analyses.

Another feature of the present invention is its applicability to any system that generates an output signal, either by virtue of a controlled or an uncontrolled input. In the latter case, it is necessary only that the output signal be generated by a subsystem of the system being examined. Thus, other parts of the same system can be analyzed for an output signal (or signals) that can serve as a control for the output signal from the subsystem of interest.

Still another feature of the present invention is its versatility. The invention can be used with substantially any types of stimulus and response, including but not necessarily limited to light, sound, temperature, pressure, aroma, taste, electric and magnetic fields, chemical and biochemical stimuli, hormonal stimuli, etc.

Yet another feature of the present invention is the ability to distinguish between the effects of the stimulus of interest and conditions (or other stimuli) that may be present. For example, the effects of subject fatigue and changes in ambient environmental conditions can be distinguished from the effects of the stimulus of interest.

Another feature of the present invention is the ability to detect and quantify output signals even when those signals form only a minuscule part of the measured signal, and even when the input is subliminal.

Other features and advantages of the present invention will be apparent to those skilled in the art from a careful reading of the Detailed Description of Preferred Embodiments presented below and accompanied by the drawings.

DETAILED DESCRIPTION OF PREFERRED EMBODIMENTS

In the following detailed description of the invention, reference numerals are used to identify structural elements, portions of elements, surfaces or areas in the drawings, as such elements, portions, surfaces or areas may be further described or explained by the entire written specification. For consistency, whenever the same numeral is used in different drawings, it indicates the same element, portion, surface or area as when first used. Unless otherwise indicated, the drawings are intended to be read together with the specification, and are to be considered a portion of the entire written description of this invention as required by 35 U.S.C. §112. As used herein, the terms "horizontal," "vertical," "left," "right," "up," "down," as well as adjectival and adverbial derivatives thereof, refer to the relative orientation of the illustrated structure as the particular drawing figure faces the reader.

Figure 1:
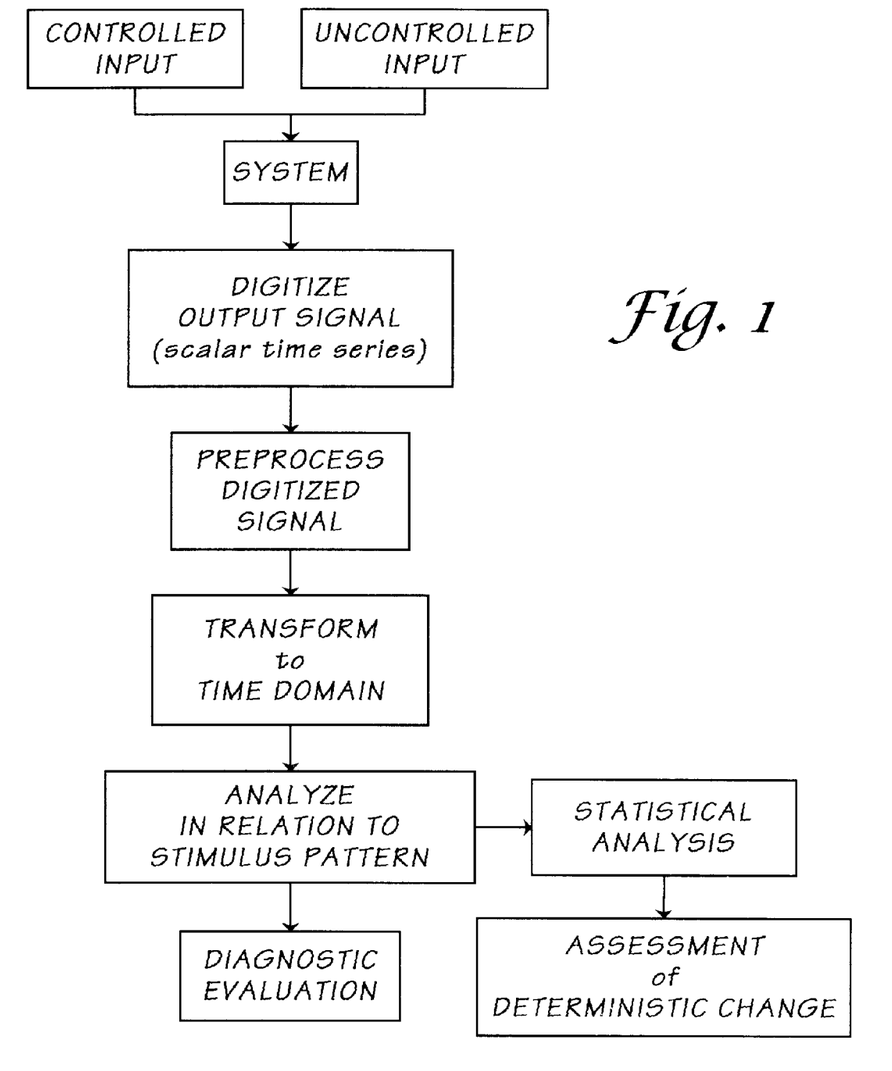
FIG. 1 is a flow chart showing a simplified view of a method according to a preferred embodiment of the present invention.

The present invention is based on the surprising discovery that Recurrence Quantification Analysis ("RQA") and related techniques can be used to quantify and analyze nonhomeostatic responses to external and internal stimuli, including but not limited to light, sound, pressure, aroma, electric and magnetic fields, chemical, biochemical, and hormonal stimuli, and internal changes on the cellular level. Briefly, a subject is exposed to a stimulus (either an external stimulus or one generated internally by the subject) while an electrophysiological signal from the subject is continuously recorded. The recorded data is digitized, stored, and analyzed using Recurrence Quantitation Analysis (RQA) and other suitable techniques. The method is implemented generally as follows (FIG. 1):

1. Expose the subject to a stimulus (light, sound, touch, aroma, taste, electric field, magnetic field, chemical, biochemical, hormonal, internal changes on the cellular level, etc.). The stimulus can be external or internal, perceivable or nonperceivable. For purposes of this detailed description, external stimuli are also referred to as "controlled inputs" and internal stimuli are also referred to as "uncontrolled inputs".

2. During exposure to the stimulus, continuously monitor and record a selected signal or signals from the subject. Suitable signals include any parameter that can be expressed as or converted to an electrical signal, including physiological variables that occur naturally as electrical signals (EEG, EKG, EMG, DC (direct current) and low-frequency AC (alternating current) signals that can be measured on the body surface, etc.). Other suitable data relate to environmental changes, chemical changes and physiological parameters that can be converted to electrical signals by suitable transducers (blood oxygen level, blood glucose, blood flow rate, blood pressure, temperature, electrical resistance, etc.).

3. Digitize the data to obtain a scalar time series.

4. Preprocess the digitized data, then analyze the data in relation to the stimulus pattern using RQA and/or other suitable techniques. The results are used to ascertain the properties of the subject's response to the stimulus. The statistical significance of the results is analyzed using any suitable test, preferably a nonparametric test such as the Wilcoxon signed rank test (however, parametric statistical techniques may also be useful). RQA techniques permit the analysis of data regardless of set size, and, importantly, assumptions regarding the statistical distribution of the data and its homogeneity (or lack thereof).

Figure 2:
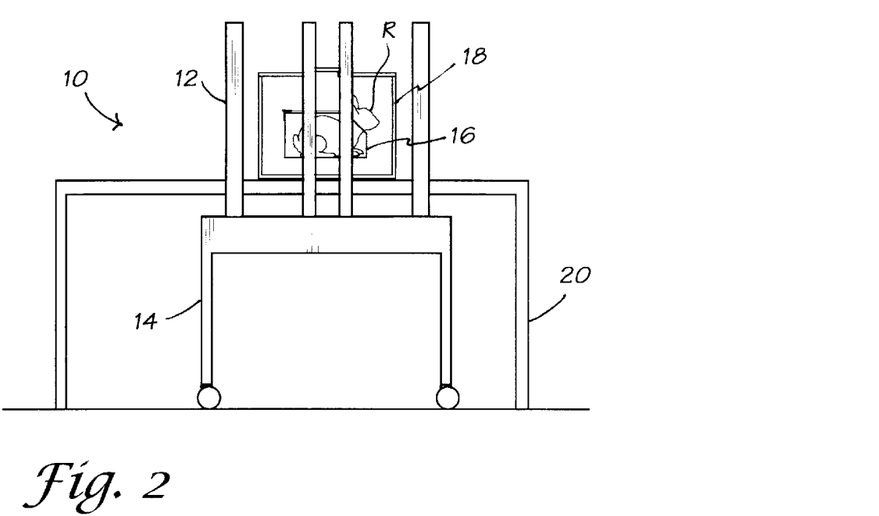
FIG. 2 is a side view of a magnetic field apparatus usable with the present invention, showing an animal containment system positioned inside the apparatus.
Figure 3:
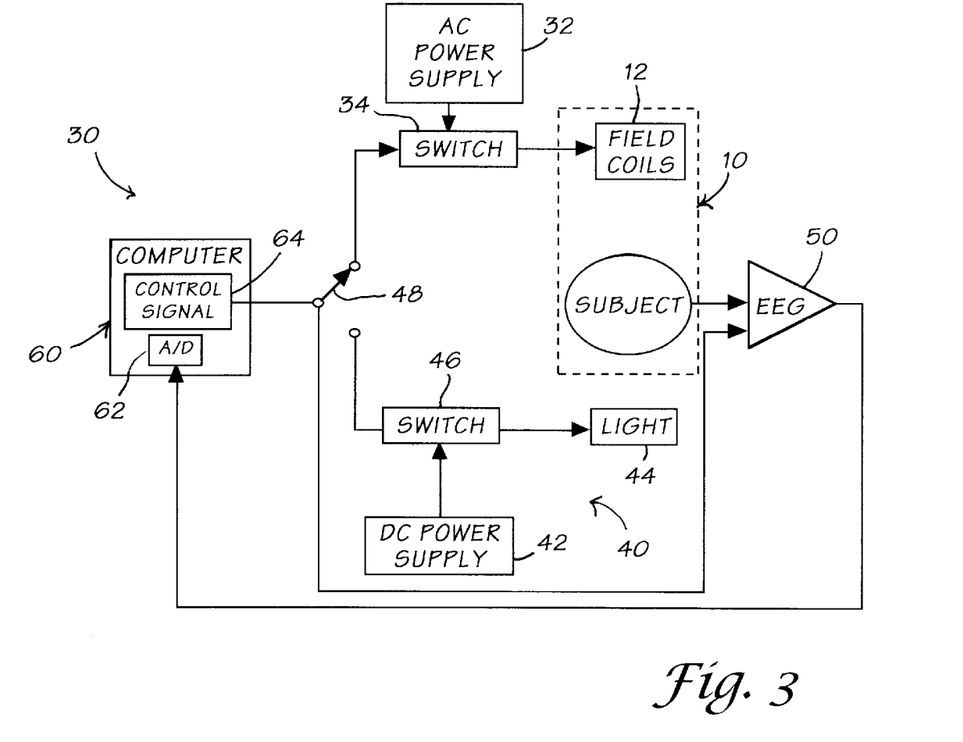
FIG. 3 is a schematic representation of an apparatus according to a preferred embodiment of the present invention, wherein controlled input stimuli (magnetic field, light) are presented to the subject.

External stimuli ("controlled inputs") may be produced by any suitable equipment; alternatively, external stimuli may be naturally-occurring events, whether perceived by the subject or not. By way of example, a magnetic field exposure system 10 usable with the present invention is shown in FIGS. 2 and 3. Magnetic fields were produced using a unit 12 of four square coils, each coil measuring 66 cm on a side and wound using 12-gauge magnet wire. The number of turns in each coil and the inter-coil spacings were chosen so that the magnetic field strength varied by less than 5% throughout the volume occupied by the animal. Unit 12 rested on a movable stand 14.

During the trials the subject (rabbit R) was restrained in an acrylic box 16 that prevented it from withdrawing its head into the box. To minimize environmental influences and standardize the rabbit's sensory environment, box 16 was mounted inside a larger wooden box 18 designed to eliminate the entry of light and minimize the entry of sound and odor, while providing for ventilation and for the passages of measurement and control signals. Box 18 was placed in unit 12, resting on a stand 20, such that the rabbit's rostral-caudal axis was approximately parallel to the unit's axis, and the rabbit was located within the homogeneous region of the magnetic field generated by unit 12. The magnetic field generated by unit 12 was a subliminal stimulus, and its presentation was not accompanied by any sensory cues.

A schematic representation of an experimental apparatus 30 is shown in FIG. 3. Apparatus 30 included magnetic field exposure system 10 with coils 12, an AC power supply 32, and a switching system 34. A weak red light served as a second controlled input, and was used as a positive control for the magnetic field stimulus generated by system 10. The light stimulus was generated by a system 40 with a DC power supply 42, an LED 44, and a switch 46. LED 44 was mounted inside box 18, approximately 10 cm from the rabbit, and produced approximately 50 lumens at the corneal surface of the eye. Selection of the stimulus (either a magnetic field generated by system 10 or a light stimulus generated by system 40) was accomplished via a switch 48.

An EEG signal from the subject (rabbit R) was measured with an EEG apparatus 50 and passed to a recording and analysis system 60, where the signal was filtered to pass 0.3–35 Hz, amplified, digitized by an A/D converter 62 at 512 Hz (12 bit), and then stored on a computer hard drive. A computer-controlled signal 64 operated switch 48 to present a stimulus to the subject.

Presentation of the stimulus (either light or a magnetic field) commenced 5 minutes after the rabbit was placed in box 16 and positioned in system 10. Each trial consisted in the application of a stimulus for 2 seconds, followed by an interstimulus period of 5 seconds. The first 5 trials were discarded, and the next 50 artifact-free trials were used for analysis of the rabbit's EEG. Results (described in Example 1 below) showed that the light stimulus caused a change in the EEG when the rabbit was conscious, and also when it was unconscious (due to administration of an anesthetic agent). The rabbit's response threshold for the magnetic field was at or below 250 mG. These results demonstrated the effectiveness of the method for studying the response of a biological system to the stimuli presented.

Figure 4:
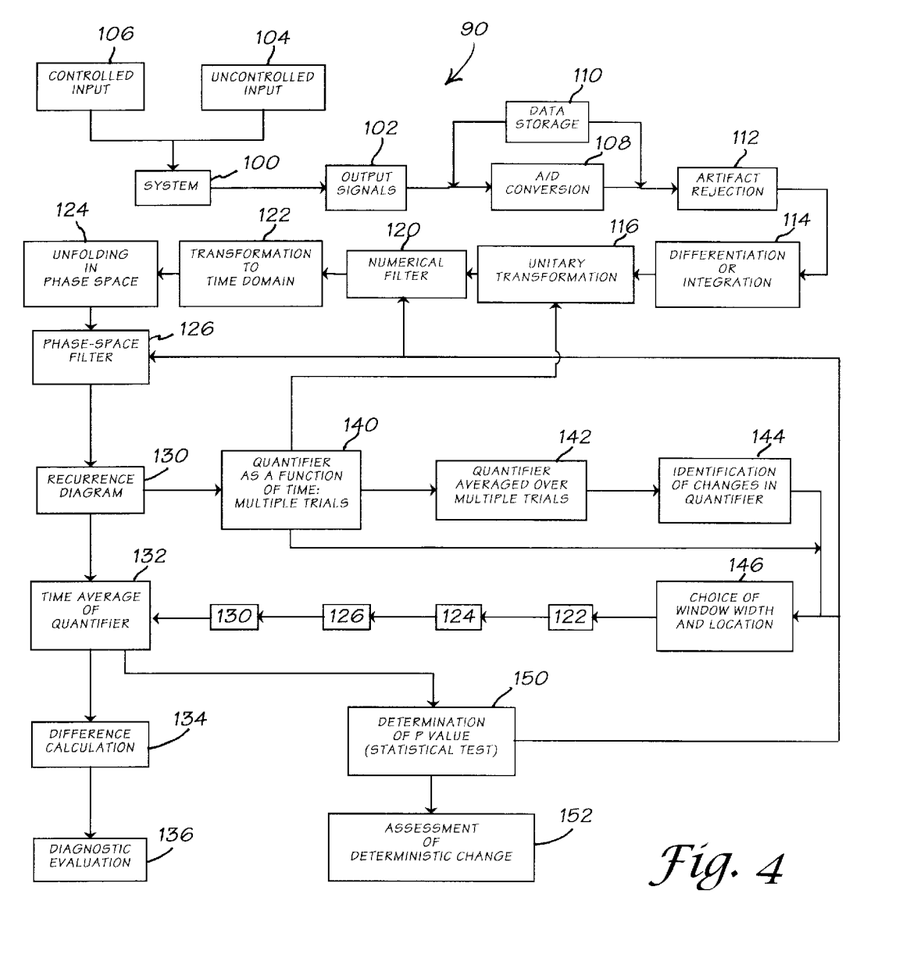
FIG. 4 is a schematic representation of a method and apparatus according to a preferred embodiment of the invention.
Figure 5:
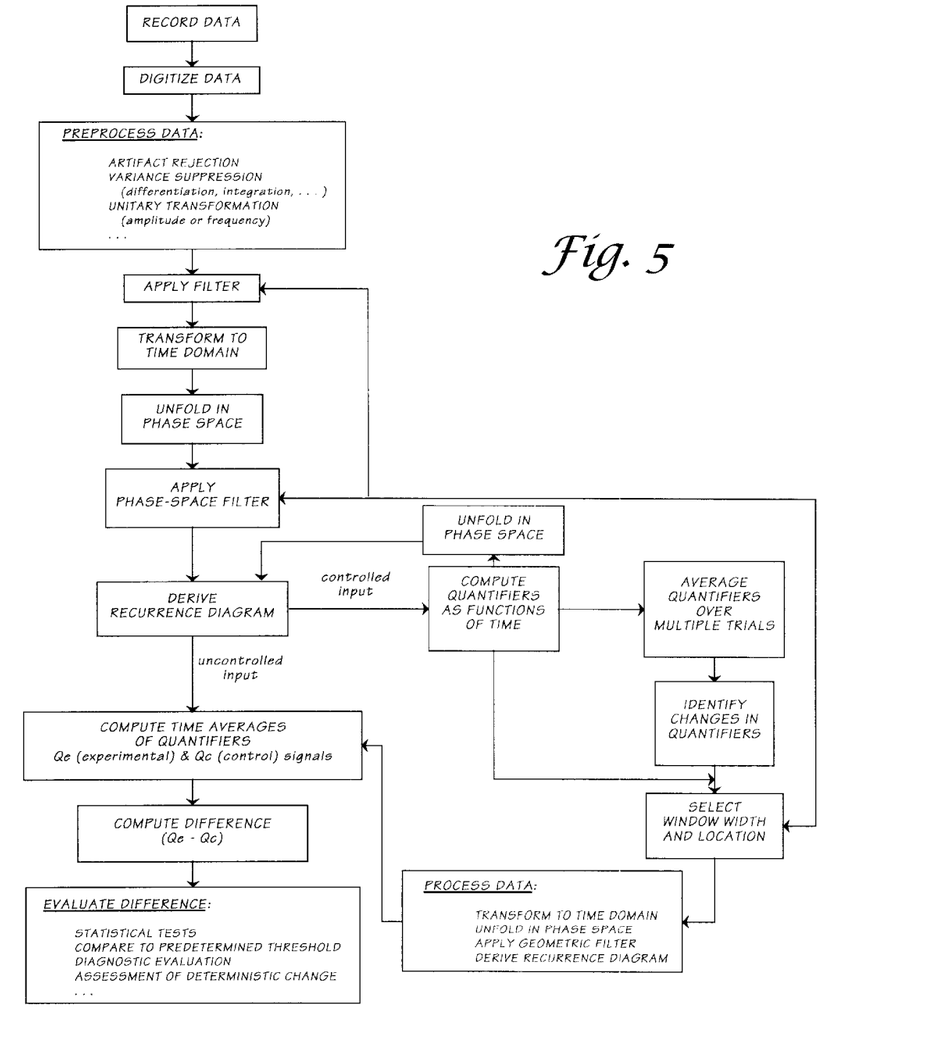
FIG. 5 is a flow chart illustrating the method of FIG. 4.

An overall schematic representation 90 of a method and apparatus according to a preferred embodiment of the present invention is shown in FIG. 4; the method is illustrated in FIG. 5. Here, a unit 100 (FIG. 4) depicts a biological or physical system from which one or more time-dependent output signals 102 can be measured. For the purpose of this detailed description, unit or system 100 is described in terms of a biological system, but it should be understood that the invention can also be used with output signals from nonbiological systems. For simplicity, the method of the invention is described assuming only one output signal 102, unless noted otherwise. However, it should be understood that the method can be used to analyze a plurality of output signals 102 generated by unit or system 100.

For purposes of this detailed description, an output signal 102 is considered to be the result of an uncontrolled input or stimulus 104 when the output is the result of spontaneous activity from a region of system 100, and when it can be analyzed in relation to spontaneous activity from other regions of the system. For example, output signal 102 could be the time-dependent voltage signal that can be measured on the surface of the skin by attaching a suitable electrode to the skin of a subject at a first location and analyzing the voltage, according to the method of this invention, in relation to a voltage similarly measured from a second, different location on the skin. Such a procedure can be used to ascertain the existence of a pathological structure at the first location, whose presence is manifested in the voltage signal measured from that location, and is recognized as such by means of a comparison with the signal from the second location.

An output signal 102 is considered to be the result of a controlled input or stimulus 106 when the output signal is measured and analyzed in relation to a specific time-dependent stimulus applied to system 100. An example is the measurement of the electroencephalogram (EEG) while a subject, considered for the purpose of this example to be a system 100, is exposed to a periodic stimulus having predetermined parameters. The EEG is measured and analyzed according to the method of this invention for the purpose of objectively establishing differences in the EEG corresponding to variations in stimulus 106, as, for example, the difference between stimulus "on" and stimulus "off" epochs. An output signal 102 may be amplified and filtered by any suitable circuits (not shown), and converted to digital form by means of an analog-to-digital (A/D) converter 108 to facilitate further processing. Alternatively, output signal 102 may be stored in a suitable storage device 110, either before or after A/D conversion, and the signal can subsequently be derived from storage device 110 and processed by the method of this invention.

Artifact rejection, applied at a unit 112, can implement a preselected or preprogrammed artifact rejection algorithm, and/or can be manually controlled through a suitable data entry device (not shown). Signal 102 may be subjected to differentiation or integration at a unit 114 to suppress elements that could interfere with subsequent analysis. For example, signal 102 may be subjected to first-differencing or higher order differencing for the purpose of removing linear trends that obscure underlying dynamical activity. Alternatively, the signal may be integrated to suppress signal variance and thereby emphasize underlying trends that might be present.

At a signal-transformation unit 116, signal 102 is subjected to a transformation into either the amplitude or frequency domain to facilitate the use of a numerical filter 120 which removes portions of the signal that interfere with the isolation of the deterministic component in the signal (in the case of controlled input 106) or with recognition of the signature component of the signal that allows diagnosis (in the case of an uncontrolled input 104). For purposes of this specification, a numerical filter is any suitable type of filter that removes selected amplitude or frequency components from the signal; alternatively, a numerical filter may remove other types of selected components from the signal. For example, the unitary transformation performed by unit 116 may be a Fourier Transformation into the frequency domain, in which case filter 120 removes one or more selected frequencies (or frequencies in one or more selected ranges), the specific identity of which would depend on the particular signal.

It has been discovered that amplitude transformations, including the wavelet transformation and other transformations known to those skilled in the art that permit a signal to be analyzed in terms of its amplitude components, can be utilized in conjunction with a numerical filter 120 to remove a range of amplitudes, thereby removing unwanted portions of the signal. For example, in the case of an output signal 102 that consists of voltage signals measured by means of electrodes attached to the skin, a 1-dimensional amplitude transformation allows identification of high-amplitude signal components that arise from the subject's heartbeat, respiration, brain electrical activity, and muscle activity, thereby allowed their removal using a suitable numerical filter 120. After this step is carried out, the small-amplitude signal components of interest can be detected.

At a unit 122 the signal is transformed back to the time domain from which it was originally derived and unfolded in a phase space 124 using mathematical methods known to those skilled in the art. A description of a suitable method is contained in "Chaos and physiology: Deterministic chaos in excitable cell assemblies," T. Elbert, W. J. Ray, Z. J. Kowalik, J. E. Skinner, K. E. Graf & N. Birbaumer, *Physiol. Rev.*, Vol. 74(1) (1994), pp. 1–47, incorporated herein by reference.

The signal is typically unfolded in a phase space having at least 3 dimensions. For example, physiological signals may be unfolded in a 5-dimensional space using a time delay of 1, but other dimensional spaces and time delays may also be useful. However, the optimum dimensions and time delay are best determined by a modest amount of experimentation for each particular application.

To increase the sensitivity of the analysis, a phase-space filter 126 is used to remove one or more non-useful portions of the signal in phase space (that is, the filter removes a selected point or points from the unfolded signal in phase space). Importantly, I have discovered that use of a phase-space filter results in a marked and surprising increase in sensitivity, analogous to the increase obtained by the use of numerical filter 120 in the domain of unitary transformation 116. For example, when controlled input 106 is the electromagnetic field from a standard cellular telephone, system 100 is a human or animal subject, and output signal 102 is the subject's EEG, excluding 10–20% of the attractor volume at its periphery is sufficient to demonstrate the deterministic effect of the electromagnetic field on the EEG.

In the case where multiple outputs are obtained at unit 102, these outputs can be used to create either one phase space, or a number of phase spaces equal to the number of outputs, as may be preferred. In the case of a plurality N of outputs, each output is time-delay embedded to obtain N phase spaces. To obtain one phase space, the N outputs are spatially embedded. In the multiple output case, the method that results in optimal sensitivity is determined empirically.

According to the present invention, use of a recurrence diagram is preferred for detecting deterministic and/or diagnostic structure in the signal after it has been passed through geometric filter 126. A recurrence diagram 130 is obtained by plotting a point in a 2-dimensional space at the location addressed by (i, j) whenever two state vectors in phase space $x_i$ and $x_j$ are near, where i and j are arbitrary index numbers. Creation of recurrence diagrams is described in "Recurrence plots of dynamical systems," J.-P. Eckmann, S. Oliffson Kamphorst & D. Ruelle, *Europhysics Letters*, Vol. 4 (1987), pp. 973–979, incorporated herein by reference. Two states are defined as "near" only if both states are contained within a hyper-geometry having a preselected radius. Typically, the radius is chosen so that it is less than 15% of the minimum radius such that all points are near, but other choices may be appropriate in particular cases.

Recurrence diagram 130 is used to derive univariate measures that characterize the deterministic and/or diagnostic structure in the signals being analyzed, and thereby provide a basis for discrimination. Univariate measures that can be derived from the recurrence diagram are known to those skilled in the art. For example, a useful description is given in "Dynamical assessment of physiological systems and states using recurrence plot strategies," C. L. Webber, Jr. & J. P. Zbilut, *J. Applied Physiology*, Vol. 76, pp. 965–973, 1994, incorporated herein by reference, wherein are described 5 univariate measures, namely, percent recurrence, percent determinism, entropy, ratio, and trend. Each quantifier may be computed and evaluated independently to assess its efficacy in affecting a discrimination between signals, or parts of signals. It is understood that, in particular cases, other quantifiers of the recurrence diagram may be used, either individually or in combination, according to the method of this invention.

Although univariate quantifiers defined on the basis of a recurrence diagram are useful measures of the deterministic behavior in the output signal 102, it is to be understood that such univariate quantifiers are described for the purpose of example and illustration; the application of the invention is not limited solely to quantifiers defined in relation to recurrence diagrams. In fact, the invention may be practiced in connection with the use of any quantifier of dynamical behavior, including but not limited to correlation dimension, Lyapunov exponent, entropy, and mutual information.

For output signals derived from uncontrolled input or inputs 104, the average value of the quantifier is computed at a unit 132 for both the output signal derived from the location of the suspected pathological change, and for the signal derived from the control location. When a difference 134 between the two values is greater than a predetermined threshold, the amount of said difference being determined empirically based on the type of underlying pathology and the nature of the physiological variable for which the recorded output signal is an appropriate surrogate, then a diagnostic evaluation 136 can be reliably made concerning the presence or absence of the putative pathology. As indicated in FIG. 5, quantifiers are denoted as "Q", with $Q_E$ identifying quantifiers for experimental or test data and $Q_C$ identifying those for control data.

In the case of a controlled input signal 106, each quantifier is calculated at a unit 140 such that the original output signal is represented by the quantifier as a function of time. Typically, controlled input 106 is applied in the context of a series of trials in which each trial consists of an epoch during which the input is applied and an epoch during which the input is not applied. At unit 140, therefore, output signal 102 is represented by a particular quantifier, and consists of a series of trials, each trial containing an exposed and control epoch. The deterministic effect produced by input signal 106 is contained within the exposed epoch, but a reliable method and procedure is required to ascertain the existence, location, and magnitude of the aforementioned deterministic effect. I have found that this goal can be achieved by following a set of iterative procedures, either individually or in combination, for particular choices of numerical filter 120 and phase-space filter 126. An iterative process, as known to those skilled in the art, is any process that carries out a series of operations repetitiously until a specified condition is met.

The output signal from the multiple trials may be time-averaged over the trials at a unit 142 to produce an increase in signal-to-noise ratio, as frequently occurs when a deterministic change occurs consistently in a linear system following application of an input. I have found that the optimal choices of quantifiers, namely those based on and derived from a recognition that the output signal 102 is partially nonlinear, permit a transformation of the output signal 102 such that the transformed signal at unit 140 displays the trial-averaging properties typically displayed by linear systems wherein an increase in signal to noise is obtained that is proportional to the square root of the number of trials averaged. Consequently, at a unit 144, it is frequently possible to identify the location, in time, of the deterministic component of the stimulus epoch by inspection of the time-averaged signal 142. For example, when controlled input 106 is an electromagnetic field of 1 G, 60 Hz, system 100 is a human being or an animal, and output signal 102 is the EEG, the percent determinism in the EEG is consistently increased approximately 200–400 msec after application of the electromagnetic field. In this case it is possible to identify the location in time of the deterministic effect of the controlled input 106 by inspection of the average results of different trials represented by 142. The portion of output signal 102 that contains the deterministic effect of controlled input 106 can then be delineated using a window 146 of known width and location, thereby facilitating a more precise analysis of the quantifier at unit 140, and thus more accurately determining the effect of controlled input 106.

Importantly, I have discovered that the dynamical activity manifested in output signal 102 of some systems 100 contains a form of nonlinear determinism that can be reflected in a quantifier at unit 140 but that is insufficiently robust, and therefore does not result in a change at unit 144 that can be determined by inspection. In these cases, the initial choice of a window width and location 146 is made arbitrarily, and both parameters are systematically varied to maximize the sensitivity of the assessment of the existence of a deterministic effect. It has been determined in this invention that a particular choice of the window width and location at 146 greatly increases the statistical reliability of the overall results.

The optimal window width and the optimal location of the deterministic effect caused by controlled input 106 and manifested in the exposure epoch of output signal 102 is ascertained by means of an iterative process in which, initially, a choice for both parameters is made, the results are ascertained, and the process is repeated to permit identification of the optimal choice as reflected in the minimum P value of the statistical test comparing the exposed and control epochs. Following a particular choice of window width and location 146, the corresponding portion of the original time domain signal from 122 is ascertained, and that portion of the signal is unfolded in phase space 124 and subjected to phase-space filter 126. A recurrence diagram is calculated for each segment of the exposed epoch, and for the corresponding segment of the control epoch. The time averaged value of the quantifier is then determined at unit 132, and the distribution of values for the quantifier obtained from the windowed segments of the exposed epoch are compared at 150 with the corresponding controls using any suitable paired statistical test, for example, the Wilcoxon signed rank test.

If the results do not achieve statistical significance, the process by which the distributions were obtained is iterated by choosing different values of numerical filter 120, phase-space filter 126, and different window widths and locations 146. The computational process is completed when the range of possible choices for all parameters has been exhausted, and a judgment of whether or not statistical significance has been achieved is made, based on the probability value of the statistical test performed, in particular, on whether statistical significance at the 5% level (or other selected level) has been achieved. Overall reliability of the procedure is insured by employing the parametric settings thus ascertained to determine whether or not a segment of a suitably chosen sham exposure epoch also results in a finding of statistical significance at the 5% level.

In particular cases, an iterative process beginning at unit 140 may be performed in which the quantifier is treated as the output signal and subjected to processing beginning at unit 116, leading to unfolding again in phase space at unit 124, calculation of a recurrence diagram at unit 130, and a quantifier at unit 140 that represents the second unfolding of the original output signal 102. The iterative process may be carried out any number of times necessary so as to reveal the deterministic structure present in the signal. The process is most useful in cases where the deterministic effect in output signal 102 does not occur in a time-locked manner within the exposed epoch, but rather occurs at different points in the exposed epochs of different trials. It is also useful in cases where the deterministic effect is relatively weak.

The present invention is further illustrated by the following nonlimiting examples.

EXAMPLE 1

Female New Zealand rabbits were exposed to controlled external inputs 106 (light, magnetic field) using above-described apparatus 30. Presentation of the stimulus (either light or a magnetic field) commenced 5 minutes after the rabbit was placed in box 16 and positioned in system 10. Each trial consisted in the application of a stimulus for 2 seconds, followed by an interstimulus period of 5 seconds. The EEG was measured using standard techniques. The first 5 trials for each rabbit were discarded; the next 50 artifact-free trials were used for analysis of the rabbit's electroencephalogram (EEG).

Each rabbit was exposed to the light stimulus and to 60-Hz magnetic fields of 0.25, 0.80, and 2.5 G in separate experiments. Every experiment was replicated at least once. As a control procedure, some of the rabbits were sacrificed and the magnetic field was applied as described above. Voltage measurements were made from the scalp electrodes to evaluate the possibility of passive electrical interactions with the electrodes.

Figure 6:
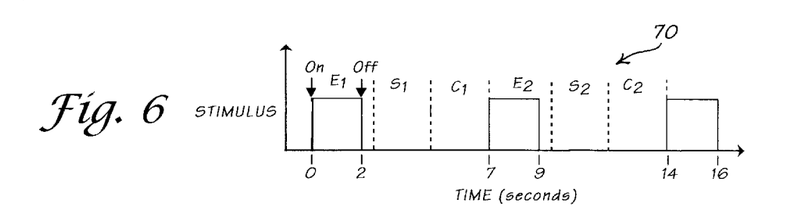
FIG. 6 is a schematic representation of two trials, showing exposed, sham and control epochs for each trial.

A schematic representation 70 of two experimental trials is shown in FIG. 6, where 2-second exposure periods ("epochs") are represented by $E_1$ and $E_2$, sham exposure epochs by $S_1$ and $S_2$, and control epochs by $C_1$ and $C_2$. The EEG measured during the last 2 seconds of each trial was used as the control for the EEG measured during the corresponding stimulation epoch. The EEG measured during the 2 seconds that preceded the control epoch was defined as the sham epoch and, as an additional control, it was analyzed statistically relative to the control in a manner identical to the analysis of the exposed epoch.

The artifact-free trials were sent through a series of numerical filters, each designed to attenuate a specific frequency band; the bands chosen were 0.3–7, 7–14, 14–21, 21–28, and 28–35 Hz. The aim of this procedure was to increase sensitivity in discrimination between exposure and control epochs by removing frequencies that did not contribute to discrimination. Preliminary studies revealed that the projected phase-space appearance of stimulus-induced changes in the EEG during the stimulation epoch (i.e., exposure period) typically lasted for several hundred milliseconds. Therefore, a procedure was undertaken using one rabbit in which only a portion of the EEG in the exposed epoch was selected for comparison with the corresponding portion of the control epoch was undertaken. The selected portion of the EEG was defined by a width and location in the epoch, and many combinations were systematically evaluated statistically in conjunction with the use of the numerical filters as described above until the window width, location, and filtering that maximized the difference between the exposed and control epochs was ascertained. The width, location, and filtering thus determined were then used for all the rabbits tested.

Figure 7A:
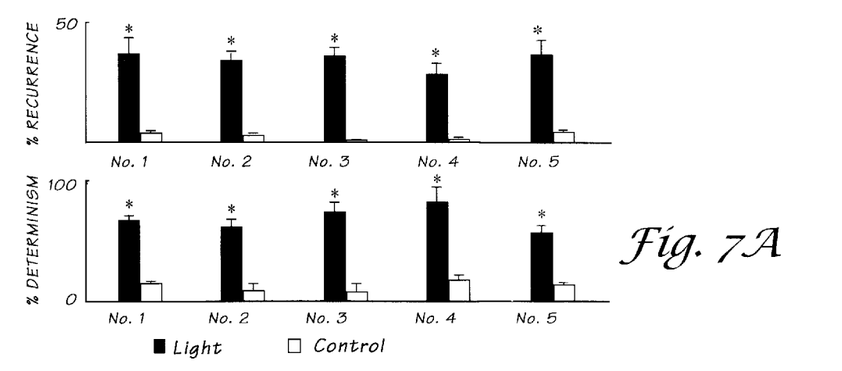
FIGS. 7A and 7B show the effects of a light stimulus and a magnetic field, respectively, on nonlinear quantifiers of brain electrical activity in rabbits.

FIG. 7A shows the effect of a 2-second light stimulus having an intensity of 50 lumens on nonlinear quantifiers of brain electrical activity (% recurrence and % determinism) in 5 rabbits (Nos. 1–5), using a window of 41–307 msec; statistically significant results ($P < 0.05$) are indicated by an asterisk (*). The results show that 50 lumens of light produced a similar change in the EEG of each rabbit. Moreover the results shown in FIG. 7A were exactly the same when each rabbit was anesthetized with ketamine hydrochloride and xylazine, proving that whether or not the rabbit was conscious did not affect the ability of light to alter brain electrical activity.

Figure 7B:
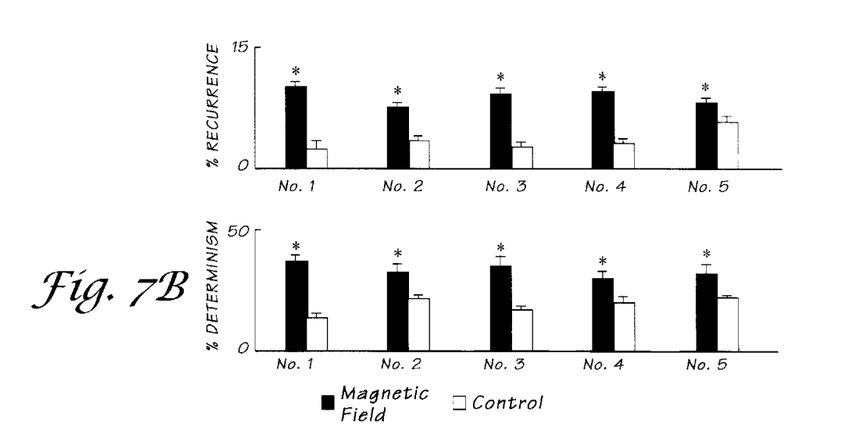

FIG. 7B shows the effect of exposure to a magnetic field (2.5 G, 60 Hz), using a window at 117–338 msec. Here, it can be seen that the response threshold was below 2.5 G because each rabbit exhibited altered EEG activity. Moreover, in contrast with the case where the stimulus was light, the magnetic field had no effect on EEG activity when the rabbits were anesthetized with ketamine hydrochloride and xylazine.

The results shown in FIGS. 7A and 7B demonstrate that the brain centers that mediate consciousness in the rabbit are crucial to the mediation of magnetic fields, but not to the mediation of light. Thus, the present invention can be used to determine which regions of the brain are primarily responsible for detecting or mediating particular stimuli.

EXAMPLE 2

Figure 8:
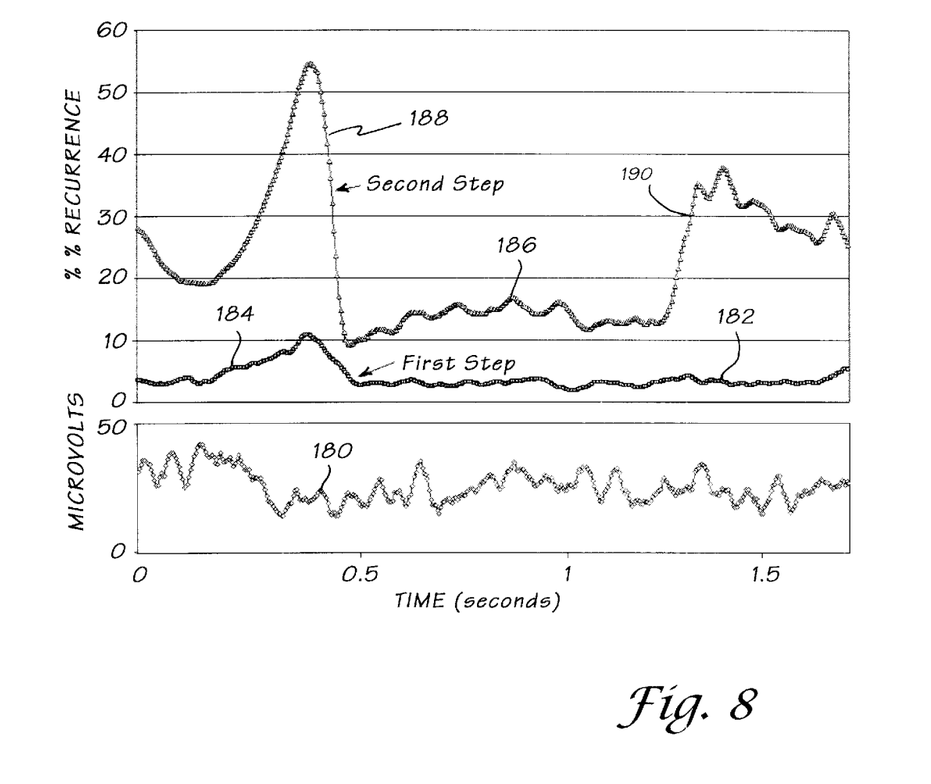
FIG. 8 shows the effects of a light stimulus on a human subject as determined using a two-step process.

A volunteer human subject was exposed to a controlled external input 106 (light) beginning at 0 time. Inspection of a typical recorded EEG signal 180 (FIG. 8) revealed no obvious change due to the presence of the light signal. Signal 180 was analyzed according to the invention as described above, revealing a change in a first percent recurrence 182 following application of the light, with the occurrence of a peak 184 at approximately 0.4 seconds. No other changes were evident. When the first percent recurrence 182 was itself treated as a signal and subjected to the recurrence analysis described above, a much stronger physiological effect in a second percent recurrence 186 was discovered: second recurrence 186 had a strong peak 188 at approximately 0.4 seconds. In addition, a previously unrecognized physiological effect (indicated at 190) occurring at approximately 1.3 seconds was revealed.

EXAMPLE 3

The operation of the present invention with an uncontrolled internal input 104 was examined. Volunteer female subjects having suspicious breast lesions or other alterations in local breast tissues suggestive of cancer (as diagnosed by mammography) were tested. Here, input 104 corresponded to the previously-diagnosed condition. Uncontrolled output signal 102 consisted of a time-dependent voltage measured on the surface of the volunteer's breast near the location of the lesion. Voltage measurements were recorded at 250 Hz for 10 minutes for each subject. Corresponding voltage measurements were made at a nearby control location.

An amplitude transformation allowed identification of high-amplitude, periodic components of output signals 102 that were due to the subject's heartbeat and respiration. These extraneous signals were removed using a suitable numerical filter 120. After this step was carried out, signals related to the electrical activity of the breast cells at or near the location of the recording electrode were evident. Results indicated that cells at or near the previously-diagnosed lesions produced different signals from nearby, presumptively normal cells. Thus, the invention permitted detection of the small-amplitude signal components that arose from the oncogenically transformed breast tissue.

The invention can be implemented using any suitable instrumentation for producing controlled inputs (if applicable), monitoring and recording controlled and/or uncontrolled inputs (as may be applicable), and monitoring and recording system outputs. For example, EEG, EMG, and EKG measurement apparatus can be used to monitor the corresponding electrophysiological signals in biological systems. Apparatus 90 may include an A/D converter (unit 108), a data storage device (unit 110), a filter or filters for artifact rejection (unit 112), a unit 114 for variance suppression, a numerical filter 120, a phase space filter 126, and a programmable computer (which may encompass some or all of units 110, 112, 120, 126, etc.) for carrying out the method, including the analysis outlined at 122–152.

It will now be evident that the invention can be used with substantially all input stimuli, whether controlled or uncontrolled, or external or internal. The input stimulus can be one that originates spontaneously from the system itself (such as oncogenically-transformed cells, localized tissue injury or inflammation, etc.), or an external stimulus (light, sound, aroma, learning task, etc.). The invention may also be used with in vitro systems and nonphysiological systems. For example, the membrane potential of cells in tissue culture constitutes an output signal that can be measured and analyzed as described above. Compressive waves sent into geological formations generate reflected waves having properties determined by the subsurface structures, and contain contributions from many kinds of subsurface structures. The invention allows the separation of these independent contributions, even though the relative contribution of the structure of interest (oil, minerals of economic interest, etc.) may be very small compared with background signals.

The method of the present invention makes it possible to reliably determine the stimulus threshold whether or not the subject is aware of the stimulus. The application of the method is independent of any underlying assumptions about the statistical distribution of the data, the homeostasis (or nonhomeostasis) of the subject and its response, and is therefore especially suited to the study of physiological systems that are characterized by nonhomeostatic transients and state changes.

With respect to the above description of the invention, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing description is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention. Thus, it will be apparent to those skilled in the art that many changes and substitutions can be made to the preferred embodiment herein described without departing from the spirit and scope of the present invention as defined by the appended claims.

What is claimed is:

1. A method for evaluating the effects of a stimulus on a system, said method comprising the steps of:

while said system is exposed to a stimulus, monitoring at least one time-dependent output signal of said system;

recording said output signal;

digitizing said recorded signal;

applying a unitary transformation to said digitized signal;

transforming said digitized signal to the time domain;

unfolding said transformed signal in phase space;

applying a filter to said unfolded signal; and deriving from said filtered signal at least one quantifier characterizing a deterministic structure of said signal.

2. The method as recited in claim 1, further comprising the step of filtering said digitized signal.

3. The method as recited in claim 2, further comprising the step of filtering said digitized signal with a numerical filter.

4. The method as recited in claim 1, wherein said unitary transformation is an amplitude or frequency transformation.

5. The method as recited in claim 1, further comprising the step of integrating or differentiating said recorded signal.

6. The method as recited in claim 1, further comprising the step of rejecting artifacts in said recorded signal.

7. The method as recited in claim 1, wherein said unfolding step is carried out using a selected time delay in a phase space having at least three dimensions.

8. The method as recited in claim 1, further comprising the step of deriving a recurrence diagram for determining said structure.

9. The method as recited in claim 1, wherein said at least one quantifier further comprises a univariate measure selected from the group consisting of percent recurrence, percent determinism, entropy, ratio, trend, correlation dimension, Lyapunov exponent, entropy, and mutual information.

10. The method as recited in claim 1, further comprising the steps of:
processing at least one control output signal of said system according to claim 1; and
comparing at least one quantifier characterizing said control signal to said at least one quantifier characterizing said unfolded signal.

11. The method as recited in claim 1, wherein said output signal corresponds to a physiological parameter, further comprising the next step of analyzing said at least one quantifier to determine a physiological state of said system.

12. The method as recited in claim 1, wherein said output signal is generated in response to a controlled input or an uncontrolled input.

13. The method as recited in claim 1, wherein said stimulus is selected from the group consisting of mechanical., electrical, electromagnetic, magnetic, thermal, hormonal, metabolic, biochemical, pharmacological, sensory, and cellular changes, and combinations thereof.

14. The method as recited in claim 1, wherein said deriving step further comprises an iterative process, said process resulting in further unfolding of said signal in phase space.

15. A method for evaluating the effects of a stimulus on a system, said method comprising the steps of:
while said system is exposed to a stimulus, monitoring at least one output signal of said system;
recording said output signal;
digitizing said recorded signal;
preprocessing said recorded signal,
applying a phase-space filter to said preprocessed signal; and
deriving from said filtered signal at least one quantifier characterizing a deterministic structure of said signal.

16. The method as recited in claim 15, further comprising the step of filtering said digitized signal with a numerical filter.

17. The method as recited in claim 16, further comprising the steps of:
applying a unitary transformation to said digitized signal;
transforming said transformed signal to the time domain, and
unfolding said transformed signal in a phase space having at least three dimensions.

18. The method as recited in claim 15, further comprising the step of suppressing variance in said recorded signal.

19. The method as recited in claim 15, further comprising the step of rejecting artifacts in said recorded signal.

20. The method as recited in claim 15, further comprising the step of deriving a recurrence diagram for determining said structure.

21. The method as recited in claim 15, wherein said at least one quantifier further comprises a univariate measure.

22. The method as recited in claim 15, wherein said output signal is generated in response to a controlled input or an uncontrolled input.

23. The method as recited in claim 15, further comprising the steps of:
processing at least one control output signal of said system according to claim 15; and
comparing said at least one quantifier characterizing said control signal to said at least one quantifier characterizing said unfolded signal.

24. The method as recited in claim 23, wherein said comparing step includes statistically analyzing said quantifiers.

25. An apparatus for evaluating the effects of a stimulus on a system, said apparatus comprising:
means for monitoring at least one time-dependent output signal of said system,
means for digitizing said output signal;
means for preprocessing said digitized signal;
phase-space filter means for removing nonuseful portions of said digitized signal; and
means for generating at least one quantifier characterizing a deterministic structure of said phase-space-filtered signal.

26. The apparatus as recited in claim 25, wherein said preprocessing means further comprises:
means for applying a unitary transformation to said signal;
numerical filter means for filtering said transformed signal; and
means for unfolding said signal in a phase space having at least three dimensions.

27. The apparatus as recited in claim 25, wherein said at least one quantifier is a univariate measure.

28. The apparatus as recited in claim 25, further comprising means for analyzing said at least one quantifier.

29. The apparatus as recited in claim 28, wherein said analyzing means includes means for statistically analyzing said at least one quantifier.

30. The apparatus as recited in claim 25, wherein said system is a physiological system, further comprising means for analyzing said at least one quantifier to determine a physiological state of said system in relation to occurrence and nonoccurrence of said stimulus.

* * * * *